US006983237B2

(12) United States Patent
Paterson et al.

(10) Patent No.: US 6,983,237 B2
(45) Date of Patent: Jan. 3, 2006

(54) METHOD AND APPARATUS FOR CONDUCTING LINKED SIMULATION OPERATIONS UTILIZING A COMPUTER-BASED SYSTEM MODEL

(75) Inventors: Thomas S. Paterson, Tiburon, CA (US); Alex L. Bangs, Watsonville, CA (US)

(73) Assignee: Entelos, Inc., Foster City, CA (US)

( * ) Notice: Subject to any disclaimer, the term of this patent is extended or adjusted under 35 U.S.C. 154(b) by 643 days.

(21) Appl. No.: 09/814,536

(22) Filed: Mar. 21, 2001

(65) Prior Publication Data

US 2001/0032068 A1 Oct. 18, 2001

Related U.S. Application Data

(63) Continuation of application No. PCT/US00/10373, filed on Apr. 14, 2000.
(60) Provisional application No. 60/129,680, filed on Apr. 16, 1999.

(51) Int. Cl.
*G06F 9/455* (2006.01)

(52) U.S. Cl. ........................................ 703/22; 717/162
(58) Field of Classification Search .................. 703/14, 703/15, 16, 2, 6, 13, 22

See application file for complete search history.

(56) References Cited

U.S. PATENT DOCUMENTS

| 4,873,623 A | 10/1989 | Lane |
| 4,881,175 A | 11/1989 | Ladner |
| 5,005,143 A | 4/1991 | Altschuler et al. |
| 5,019,961 A | 5/1991 | Addesso et al. |

(Continued)

OTHER PUBLICATIONS

Malkamaki et al., E. A Method for Combining Radio Link Simulations and System Simulations for a Slow Frequency Hopped Cellular System, 1994 IEEE 44th Vehicular Technology Conference, pp. 1145–1149.*
Johansson, B.C.V. Packet Data Capacity in a Wideband CDMA System, VTC 98, 48th IEEE Vehicular Technology Conference, 1998, vol. 3, pp. 1878–1883.*
Devetsikiotis et al., M. A Dynamic Importance Sampling Methodology for the Efficient Estimation of Rare Event Probabilities in Regenerative Simulations of Queueing Systems, IEEE International Conference on Communications, 1992, ICC '92, pp. 1290–1296.*
Abrams et al., M. Linking Simulation Model Specification and Parallel Execution Through UNITY, IEEE Simulation Conference, Winter 1991, pp. 223–232.*
*ModelMaker Reference*, Cherwell Scientific Limited, Apr. 2000.
"ModelMaker 2.0 for windows", Mark Bernard, *Biotechnology Software Journal*, Nov./Dec. 1995, pp 16–19.

(Continued)

*Primary Examiner*—Russell Frejd
(74) *Attorney, Agent, or Firm*—Schwegman, Lundberg, Woessner & Kluth, P.A.

(57) ABSTRACT

A method of conducting a sequence of linked simulation operations, utilizing a computer-based simulation model, commences with the performance of a first simulation operation to generate an output condition. A further simulation operation, which is defined to sequentially follow the first simulation operation, is then formed utilizing the simulation model. The second simulation operation at least partially and automatically inherits the output condition generated by the first simulation operation as an input condition. In this way, the second simulation operation commences with a configuration captured from a preceding simulation operation as an input condition. Multiple simulation operations may at least partially inherit a configuration from the first simulation operation.

23 Claims, 11 Drawing Sheets

U.S. PATENT DOCUMENTS

| | | | |
|---|---|---|---|
| 5,081,584 | A | 1/1992 | Omichinski et al. |
| 5,111,413 | A * | 5/1992 | Lazansky et al. ............. 703/14 |
| 5,257,364 | A | 10/1993 | Melamed et al. |
| 5,307,287 | A | 4/1994 | Cramer, III et al. |
| 5,307,479 | A | 4/1994 | Ulrich et al. |
| 5,331,573 | A | 7/1994 | Balaji et al. |
| 5,408,638 | A | 4/1995 | Sagawa et al. |
| 5,418,944 | A | 5/1995 | DiPace et al. |
| 5,424,963 | A | 6/1995 | Turner et al. |
| 5,428,740 | A | 6/1995 | Wood et al. |
| 5,434,796 | A | 7/1995 | Weininger |
| 5,463,564 | A | 10/1995 | Agrafiotis et al. |
| 5,466,321 | A | 11/1995 | Miyaji |
| 5,481,741 | A | 1/1996 | McKaskie et al. |
| 5,485,600 | A | 1/1996 | Joseph et al. |
| 5,495,423 | A | 2/1996 | DeLisi et al. |
| 5,526,281 | A | 6/1996 | Chapman et al. |
| 5,535,422 | A | 7/1996 | Chiang et al. |
| 5,544,067 | A | 8/1996 | Rostoker et al. |
| 5,555,201 | A | 9/1996 | Dangelo et al. |
| 5,566,295 | A | 10/1996 | Cypher et al. |
| 5,574,854 | A | 11/1996 | Blake et al. |
| 5,623,418 | A | 4/1997 | Rostoker et al. |
| 5,640,549 | A | 6/1997 | Powsner et al. |
| 5,657,255 | A | 8/1997 | Fink |
| 5,680,590 | A | 10/1997 | Parti |
| 5,692,184 | A | 11/1997 | Ardoin et al. |
| 5,715,413 | A | 2/1998 | Ishai et al. |
| 5,729,466 | A | 3/1998 | Bamji et al. |
| 5,732,192 | A | 3/1998 | Malin et al. |
| 5,732,277 | A | 3/1998 | Kodosky et al. |
| 5,737,581 | A | 4/1998 | Keane |
| 5,737,727 | A | 4/1998 | Lehmann et al. |
| 5,757,678 | A | 5/1998 | Leeke |
| 5,784,593 | A * | 7/1998 | Tseng et al. .................. 703/15 |
| 5,808,918 | A | 9/1998 | Fink et al. |
| 5,809,283 | A * | 9/1998 | Vaidyanathan et al. ....... 703/16 |
| 5,815,415 | A | 9/1998 | Bentley et al. |
| 5,845,124 | A | 12/1998 | Berman |
| 5,872,957 | A | 2/1999 | Worthington et al. |
| 5,956,501 | A | 9/1999 | Brown |
| 5,963,724 | A | 10/1999 | Mantooth et al. |
| 5,987,243 | A | 11/1999 | Aihara |
| 6,051,029 | A | 4/2000 | Paterson et al. |
| 6,063,128 | A | 5/2000 | Bentley et al. |
| 6,078,739 | A | 6/2000 | Paterson et al. |
| 6,236,956 | B1 | 5/2001 | Mantooth et al. |
| 6,246,975 | B1 | 6/2001 | Rivonelli et al. |
| 6,289,299 | B1 | 9/2001 | Daniel, Jr. et al. |
| 6,324,495 | B1 | 11/2001 | Steinman |
| 6,539,347 | B1 | 3/2003 | Paterson et al. |

OTHER PUBLICATIONS

"Ruminations of a Model Maker", Dick Lundin, *IEEE Computer Graphics*, May 1987, pp. 3–5.

*ModelMaker User Manual*, Cherwell Scientific Limited, Apr. 2000, pp111–115.

"About ModelMaker", ModelKinetix.com, www.modelkinetix.com/modelmaker/index.htm, no date given.

"Modelmaker 3.0 for Windows", Mario J. Citra, May 7, 1997, *J. Chem Inf. Comput Sci.*, vol 37, No. 6, 1997, pp 1198–1200.

"ModelMaker for windows version 3", *Oxford: Cherwell Scientific 1997*, 499 Serial No. 110 302 1161 R, no additional date given.

"Appendix E Generic Library Blocks", *Extend, Performance Modeling for Decision Support, User's Manual*, Imagine That, Inc.,(1994),361–403.

"Chapter 1 Running a Model", *Extend, Performance Modeling for Decision Support, User's Manual*, Imagine That, Inc.,(1994),11–24.

et al., "Chapter 1 Introduction to Model–Based Diagnosis", *Readings in Model–Based Diagnosis*, Hamscher, W., et al., Editors, Morgan Kaufmann Publishers,(1992),1–2.

"Chapter 1 Objects", *Powersim 2.5, Reference Manual*, Powersim Corporation,(1996),1–1 to 1–41.

"Chapter 12 Statistical Interference", *Mathematical Modeling in the Life Sciences*, Docet, P., et al., Editors, Ellis Horwood Ltd.,(1992),239–274.

"Chapter 12 The Simulation Algorithms", *ithink The Visual Thinking Tool for the 90's—Technical Reference*,(1994), 12–1 to 12–13.

"Chapter 13 Working With Models", *Mathematical Modeling in the Life Sciences*, Doucet, P., et al., Ellis Horwood Ltd.,(1992),275–298.

"Chapter 14 Constructing Models", *Mathematical Modeling in the Life Sciences*, Doucet, P., Editors, et al., Ellis Horwood Ltd.,(1992)299–324.

"Chapter 2 Building a Model", *Extend, Performance Modeling for Decision Support, User's Manual*, Imagine That, Inc.,(1994),25–46.

"Chapter 2 Building and Simulating Models", *Powersim 2.5, User's Guide*, Powersim Corporation,(1996),11–37.

"Chapter 2 Stocks & Flows, Infastructure and Feedback Loops", *ithink The Visual Thinking Tool for the 90's, Introduction to Systems Thinking and ithink*. High Performance Systems, Inc.,25–38.

"Chapter 3 Basic Building Blocks", *ithink The Visual Thinking Tool for the 90's, Introduction to Systems Thinking and ithink*, High Performance Systems, Inc.,(1994),39–64.

"Chapter 4 Building Blocks", *ithink The Visual Thinking Tool for the 90's, Technical Reference*, High Performance System, Inc.,(1994),4–1 to 4–36.

"Chapter 4 Using the Generic and Discrete Event Libraries", *Extend, Performance Modeling for Decision Support, User's Manual*, Imagine That, Inc.,(1994),69–102.

"Chapter 5 Using Powersim Objects", *Powersim 2.5, User's Guide*, Powersim Corporation,(1996),79–99.

"Chapter 6 Input and Output", *Extend, Performance Modeling for Decision Support, User's Manual*, Imagine That, Inc.,(1994),113–137.

"Chapter 8—Using Graphs", *Mathematical Modeling in the Life Sciences*, Doucet, P., et al., Editors, Ellis Horwood Ltd.,(1992),155–168.

"Chapter 8 Guidelines for the Modeling Process", *Ithink The Visual Thinking Tool for the 90's, Introduction to Systems Thinking and ithink*, High Performance Systems, Inc., (1994),152–154.

"User Interface to Support Multiple Actions Within a Connection", *IBM Technical Disclosure Bulletin*, 37(7), (Jul. 1, 1994),379.

Aliev, M. K., et al., "Mathematical Modeling of Intercellular Transport Processings and the Cretine Kinase Systems: A Probablity Approach", *Molecular and Cellular Biochemistry*, 133/134, (Apr.–May, 1994),333–346.

Berger, M. P., et al., "Combining Statistical, Rule–Based, and Physiologic Model–Based Methods to Assist in the Management of Diabetes Mellitus", *Computer and Biomedical Research*, 23(4), (1990),346–357.

Cellier, F. E., "Qualitative Modeling and Simulation: Promise or Illusion", *Proceedings of the 1991 Winter Simulation Conference*,(1991),1086–1090.

Clancey, W. J., "Viewing Knowledge Bases as Qualitative Models", *IEEE Expert, Tools and Techniques*, 4(2), (Summer 1989),9–23.

Conolly, R. B., "Biologically Based Pharmacodynamic Models: Tools for Toxicological Research and Risk Assessment", *Annual Review of Pharmacology and Toxicology*, 31, (1991),503–523.

Conolly, R. B., et al., "Computer Simulation of Cell Growth Governed by Stochastic Processes: Application to Clonal Growth Cancer Models", *Toxicology and Applied Pharmacology*, 124(2), (1994),284–295.

Davis, R., "Reasoning from First Principles in Electronic Troubleshooting", *International Journal of Man–Machine Studies*, 19 (1983),403–423.

Fishwick, P. A., "Qualitative Methodology in Simulaton Model Engineering", *Simulation*, 52(3), (1989),95–101.

Forbus, K. D., et al., "Qualitative Process Theory", *Artificial Intelligence*, 23, (1984),85–168.

Hoang, K. T., et al., "Physiologically Based Pharmacokinetic Models: Mathematical Fundamentals and Simulation Implementations", *Toxicology Letters*, 79(1–3), (1995),99–106.

Hunt, N., "IDF: A Graphical Data Flow Programming Language for Image Processing and Computer Vision", *Proceedings of the International Conference on Systems, Man and Cybernetics*, (1995),351–360.

Karp, P. D., et al., "Chapter 7: Coordinating the Use of Qualitative and Quantitative Knowledge in Declarative Dveice Modeling", *In: Artificial Intelligence, Simulation and Modeling*, John Wiley & Sons, Inc., Publishers,(1989), 189–206.

Kuipers, B., "Qualitative Process Theory", *Artificial Intelligence,* 29, (1986),289–388.

Lin, Y.–B., et al., "A Flexible Graphical User Interface for Performance Modeling", *Software Practice & Experience*, 25(2), (1995),193–216.

Patil, R. S., et al., "Casual Understanding of Patient Illness in Medical Diagnosis", *Proceedings of the International Joint Conference on Artificial Intelligence (IJCAI)*, (1981), 893–899.

Sieburg, H. B., et al., "Chapter 65—The CyberMensch Simulation Server for the Planning of Clinical Trials", *In: Interactive Technology and the New Paradign for Healthcare*, R. M. Satava, et al., Editors, IOS Press, Publishers, (1995),445–454.

Sieburg, H. B., "In Silico Environments Augment Clinical Trials", *IEEE Engineering in Medicine and Biology*, 15(2), (1996),47–59.

Sieburg, H. B., "Methods in the Virtual Wetlab I: Ruled–n–Based Reasoing Driven by Nearest–Neighbor Lattice Dynamics", *Artificial Intelligence in Medicine*, 6(4), (1994), 301–319.

Barra, A., et al., "Knowledge–Based Simulation, Alfred Round–Intelligent Interfaces", *The Handbook of Artificial Intelligence, vol. 4, Chapter 22*, (Dec. 1989),415–518.

\* cited by examiner

METHOD AND APPARATUS FOR CONDUCTING LINKED SIMULATION OPERATIONS UTILIZING A COMPUTER-BASED SYSTEM MODEL

The present application is a continuation of PCT patent application No. PCT/US00/10373 entitled "METHOD AND APPARATUS FOR PERFORMING A LINKED EXPERIMENT SEQUENCE", filed Apr. 14, 2000, which claims priority from U.S. provisional patent application No. 60/129,680 entitled "METHOD AND APPARATUS FOR PERFORMING A LINKED EXPERIMENT SEQUENCE", filed Apr. 16, 1999.

FIELD OF THE INVENTION

The present invention relates generally to the field of computer-based simulations and, more specifically, to the linking of a sequence of simulations operations performed utilizing a computer-based system model.

BACKGROUND OF THE INVENTION

Simulation and modeling software typically allows a model operator to perform simulation operations over a specified time interval, each simulation operation utilizing specified inputs (e.g., rate constants and initial conditions) to generate specific outputs over the time interval for the operation. However, prior art simulation models, and interfaces for specifying simulations operations performed by such simulation models, do not provide a convenient mechanism for specifying a sequence of simulation operations whereby each operation in that sequence may employ varying inputs (e.g., rate constants) or a resetting of the state (initial conditions) of the modeled system.

SUMMARY OF THE INVENTION

According to the invention, there is provided a method of conducting a sequence of linked simulation operations utilizing a computer-based model. A first simulation operation is performed utilizing the model to generate an output condition for the model. A plurality of further simulation operations are performed utilizing the model. Each such further simulation operation at least partially and automatically inherits the output condition, generated by the first simulation operation, as an input condition.

In one embodiment, at least one of the plurality of further simulation operations automatically utilizes a delta condition, in conjunction with a subset of the output condition of the first simulation operation, as the input condition.

Other features of the present invention will be apparent from the accompanying drawings and from the detailed description that follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and apparatus for conducting a sequence of linked simulation operations utilizing a computer-based model are described. In the following description, for purposes of explanation, numerous specific details are set forth in order to provide a thorough understanding of the present invention. It will be evident, however, to one skilled in the art that the present invention may be practiced without these specific details.

For the purposes of the present specification, the term "parameter" shall be taken to include, but not be limited to, a variable or an arbitrary constant that may appear in a mathematical expression (e.g., an equation).

Figure 1:
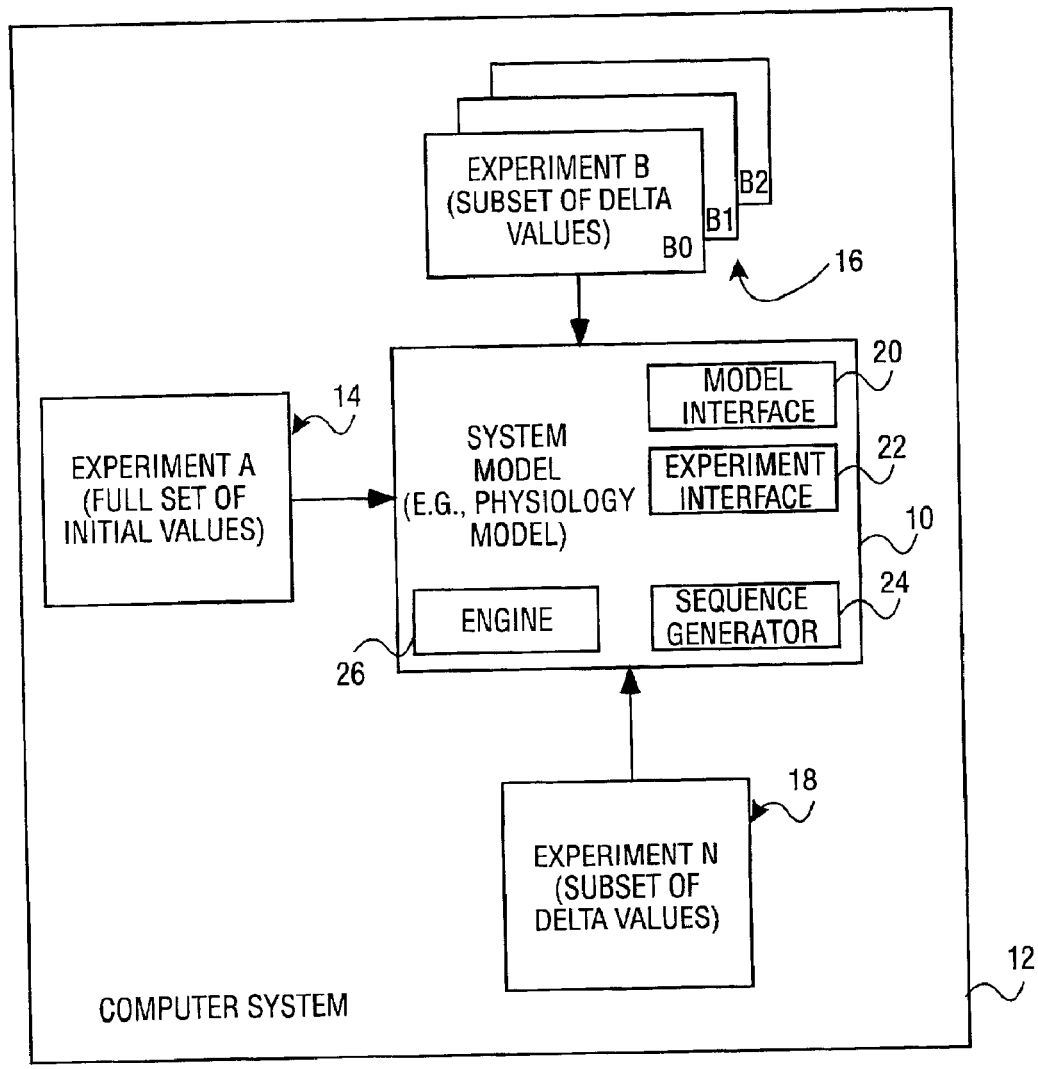
FIG. 1 is a block diagram illustrating an exemplary computer-based system model that executes on a computer system to perform simulation operations.

FIG. 1 is a block diagram showing an exemplary computer-based system model 10 that executes on a computer system 12 to perform simulation operations. The system model 10 may be constructed utilizing any one of number of commercially available modeling tools to model a wide variety of systems. Such modeling tools may include tools provided by Entelos, Inc. of Menlo Park, Calif. Other commercially available modeling tools include the Process Charter of Scitor Corporation of Menlo Park, Calif., PowerSim developed by Modell Data AS of Bergen, Norway, the ithink and Stella tools developed by High Performance Systems Incorporated of Hanover, N.H., and the Extend+ BPR developed by Imagine That! Incorporated of San Jose, Calif.

The below description shall describe an exemplary embodiment where the system model 10 comprises a physiology model that simulates the physiology of diseases (e.g., asthma, obesity, HIV-AIDS or diabetes). Nonetheless, it will be appreciated that the system model 10 may model any number of systems, including but not limited to physiological, mechanical, environmental, chemical, biological, electrical or physical systems.

A number of collections of protocols and parameters in the form of experiments 14, 16 and 18 are shown to provide input to the system model 10. While the inputs to the system model 10 are labeled "experiments", these inputs need not necessarily comprise experiments, but may be any collection of protocols and/or values that provide input and/or initial state to the system model 10. In the exemplary embodiment where the system model 10 comprises a physiology model, the experiments 14, 16 and 18 constitute distinct sets of conditions (e.g., environment or system conditions) that are imposed upon the system model 10 to determine performance of the system model 10 under these conditions. A first experiment 14, for example, includes a full set of initial values (or conditions) that define a first experimental condition, the second experiment 16 constitutes a subset of delta values and any number of further experiments 18 may constitute further subsets of delta values for various parameters of the system model 10. In the exemplary embodiment, the experiments 14, 16 and 18 are a linked, sequence of experiments that, as will be described in further detail below, may partially inherit an output condition (e.g., parameter values) from a preceding experiment and impose delta values on other parameters to thereby define a new experimental condition (or configuration) that has some dependencies upon the output of a previous experiment. It is further envisaged that any of the experiments 14, 16 and 18 may utilize, or at least partially inherit, an output condition, or parameters, from any of the other experiments. For example, both experiment 16 and any number of experiments 18 may inherit an output condition from experiment 14. Alternatively, experiment 16 may inherit a partial output condition from experiment 14, and experiment 18 may inherit a partial output condition from experiment 16. Further details in this regard shall be provided below.

The system model 10 is also shown to include a model interface 20 via which a modeler may define the system model 10 and an experiment interface 22, to be described in further detail below, via which a modeler may define, or modify, an experiment performed utilizing the system model 10.

Figure 2:
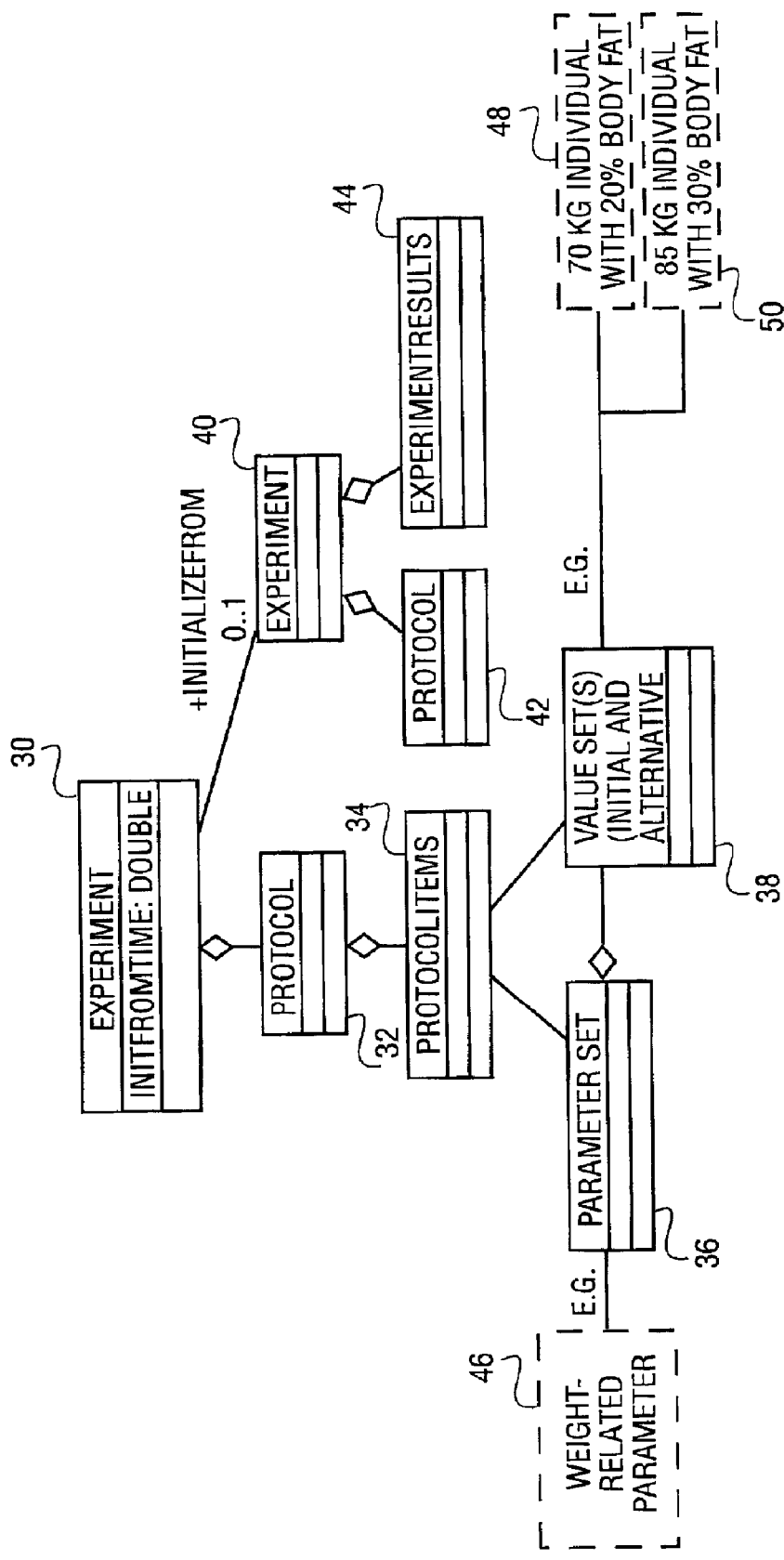
FIG. 2 is an inheritance diagram illustrating structure of an exemplary experiment class.

FIG. 2 is an inheritance diagram illustrating the components of an exemplary experiment class 30 that may comprise any of the experiments 14, 16 and 18 shown in FIG. 1. Specifically, an experiment class 30 is shown to own one, or multiple, protocol classes 32, each of which may include zero, one, or multiple protocol items 34. Each protocol item 34 references a parameter set 36 and value set 38 pair. The value set 38 in the protocol item 34 is constrained to only those value sets 38 owned by the parameter set 36. For example, an exemplary parameter set 36 a particular experiment may be weight-related parameters 46 and may own a number of user-selectable value sets such as the "70% kg individual with 20% body fat" value set 48 and the "85 kg individual with 30% body fat" value set 50.

An experiment 40, related to the experiment class 30, is accordingly shown to own one or more protocols 42 and a set of experiment results 44 that constitute the output of the system model 10, where the protocol 42 has specified a particular parameter set 36 having one or more value sets 38 attributed thereto. If an experiment 30 has an initial experiment 40, then the parameter INITFROMTIME contains the time to get values for time-varying parameters for experiment 30 from the experiment results 44 in experiment 40.

Figure 3:
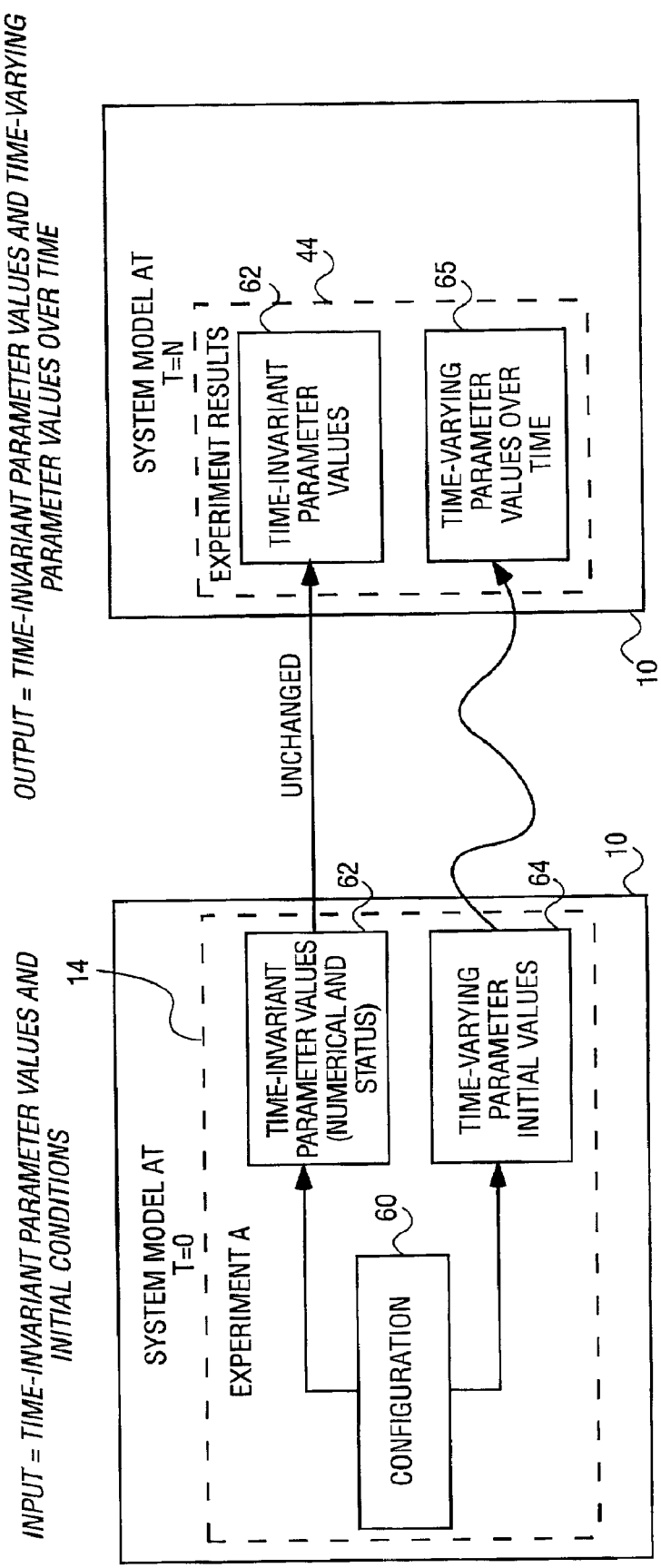
FIG. 3 is a diagrammatic representation of the performance of an exemplary simulation operation, in the form of an experiment, over a predetermined time period.

FIG. 3 is a diagrammatic representation of the performance of a simulation operation, such as for example an experiment, over a predetermined time period. At a first time instance (e.g., T=0), the system model 10 is shown to be initialized with the experiment 14. The experiment 14 embodies a configuration 60. The configuration 60 includes time-invariant parameter values 62 that remain unchanged over the simulation operation and a set of time-varying parameter initial values 64 that are modified as a result of the simulation operation. For example, the time-varying parameter initial values 64 may be integrated over the time interval of the simulation operation.

Accordingly, after a predetermined time interval (e.g., T=N), the time-invariant parameter values 62, and the modified time-varying parameter values over time 65, are shown to constitute the experiment results 44 of the experiment 14 at the predetermined time (e.g., T=N). The experiment results 44 thus constitute a set of values for a set of model parameters that define an output condition of the experiment 14.

Figure 4:
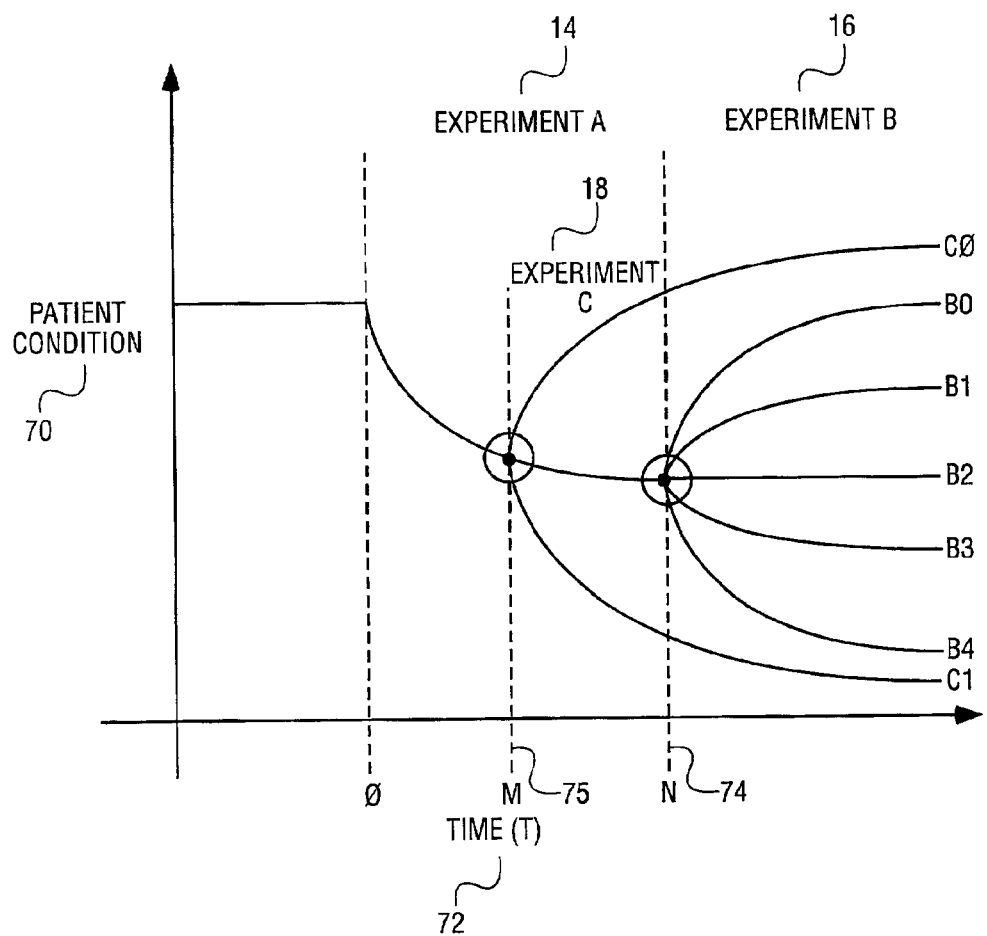
FIG. 4 is a block diagram plotting a value for a time-variant parameter of the system model shown in FIG. 1.

FIG. 4 is a plot diagram that plots a value for a time-varying parameter of the system model 10 included in both experiment 14 and experiment 16 over time. The exemplary parameter is identified as being a patient condition parameter 70, being any parameter indicative of a patient's condition plotted against time 72. During performance of the simulation operation of experiment 14, the patient condition parameter 70 is shown to decline with time until a time N 74 is reached. The values for the various parameters of the experiment 14 (both time-invariant and time-varying) at time N 74 thus constitute the experiment results 44 of experiment 14.

An experiment 16 is shown to then commence at time N 74 and at least partially inherits the output condition (e.g., the experiment results 44) of the experiment 14 plus the time-invariant parameter values 62 from the experiment 14 as an input condition (e.g., as a configuration 60). Further, the experiment 16 may, in addition to the inherited values for various parameters, specify a set of delta values for a subset of parameters that represent a delta condition. For example, experiment 16 may, as a delta condition, introduce a specific drug treatment that was not present in experiment 14, so that the effect of this drug treatment on the patient condition parameter 70 may be monitored over time. A number of experiments 16, each introducing a different delta condition (e.g., a different drug treatment), may at least partially utilize the output condition of the experiment 14 as an input condition (or configuration).

While in one embodiment, a plot diagram, such as that shown in FIG. 4, may be generated as a result of a sequence of linked experiments, or as results of a single experiment to which multiple protocols are applied, such a plot diagram may also be generated for discrete experiments that are not defined as being linked or sequenced. For example, a plot diagram such as that shown in FIG. 4 may be generated where the experiment results for experiment 14 are manually saved, and then copied or at least partially introduced as a configuration 60 for experiment 16. Accordingly, the plot diagram shown in FIG. 4 is not dependent upon a continuous, seamless and pre-sequenced set of experiments or protocols. According to one embodiment of the present invention, such a plot diagram may be generated for multiple simulation operations (e.g., experiments), that are manually linked.

The plot diagram illustrated in FIG. 4 is advantageous in that it allows a modeler, in a convenient manner, to view one or more parameters included in one or more experiments (or protocols) that are linked either in a predefined-manner for automatic linkage, or that are linked manually by a modeler who copies experimental results for a preceding experiment for utilization as a configuration 60 for a subsequent experiment.

It should also be noted that the diagrammatic plot shown in FIG. 4 may plot values for at least one parameter for multiple experiments (e.g., multiple experiments 16) that may be linked to, and received configuration conditions from, a preceding experiment (e.g., experiment 14). Thus, FIG. 4 illustrates multiple plots for the patient condition 70 at B0–B4, each of the plots B0–B4 being generated as a result of a linked experiment 16 (or protocol). In this way, a modeler may conveniently be presented with a visual comparison of the effect of various experiment and protocol conditions on a particular experiment parameter (or parameters) for a common initial condition or configuration.

The present invention contemplates linking experiment 14 and one or more further experiments 16, so that the further experiments 16 seamlessly and automatically inherit an output condition of a first experiment 14 as an input condition. In this way, by linking a sequence of experiments, it is possible to create a history for a modeled system (e.g., a physiology system). Input conditions that constitute the output of a first experiment do thus not have to be restated for each of the further experiments 16, and outputs of the experiment 14 are automatically and seamlessly considered in linked, dependent experiments 16. A single experiment sequence, for example including experiment 14 and experiment 16, may be defined in a single experiment through the use of multiple protocols per experiment. Specifically, experiments 14 and 16, in one embodiment, need not be regarded or defined as separate or distinct experiments. In this case, a protocol variation may be introduced at time N 74. The multiple protocols may, in one example, be defined to each become active at varying times throughout the relevant experiment.

It should be noted that a sequence of any number of experiments may be defined, with each experiment at least partially, or even completely, utilizing the output condition of a preceding experiment as an input condition. Furthermore, multiple experiments may be defined to utilize the output of a preceding experiment as an input condition. For example, multiple experiments 16 are shown in FIG. 4 to utilize the output of experiment 14 as an input condition, with each of the experiments 16 introducing a different delta condition. Each of multiple experiments 16 may also choose a different time than N 74, as long as the time is less than or equal to the duration of the preceding experiment 14. For example, experiment C is shown to utilize the output of experiment 14 at a different time (i.e., time M 75) as an input condition. This illustrates that multiple experiments may utilize a state, or conditions, of a first experiment at different times as input to such further experiments.

Each of the multiple experiments 16 may, in one embodiment, be performed seamlessly and automatically on conclusion of the preceding experiment 14. In this case, a graphical plot, such as that illustrated in FIG. 4, may automatically be displayed on a display device associated with a computer system to communicate a particular parameter condition to a modeler for each of the multiple experiments 16.

Figure 5:
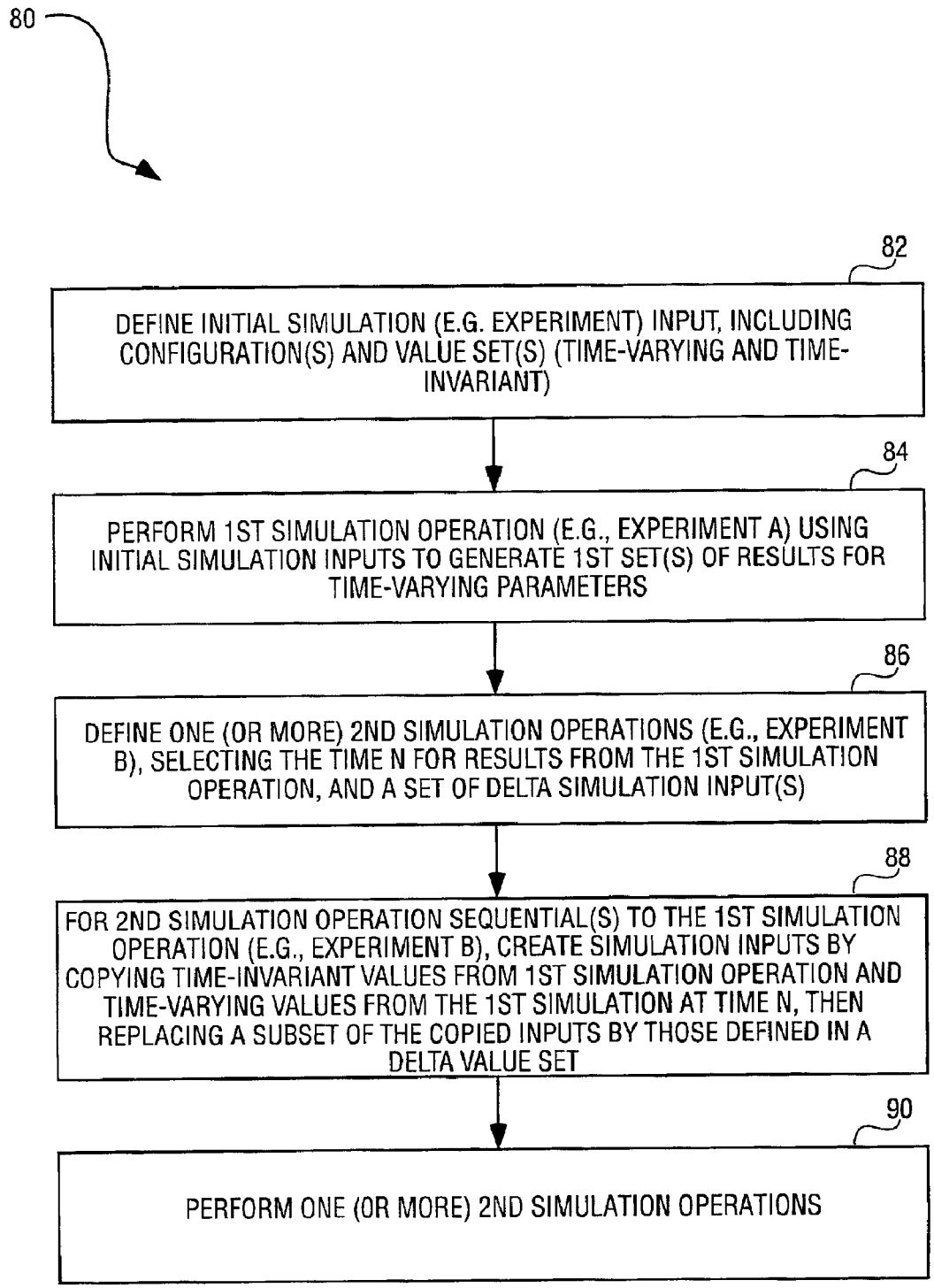
FIG. 5 is a flowchart illustrating a method, according to an exemplary embodiment of the present invention, of conducting sequential simulation operations utilizing the system model.

FIG. 5 is a flow chart illustrating a method 80, according an exemplary embodiment of the present invention, of conducting sequential simulation operations utilizing the system model 10. The method 80 commences at block 82 with the definition of an initial simulation operation (e.g., the experiment 14). The definition of the initial simulation operation may include defining one or more parameter sets 36 for the experiment 14, and also selecting, inputting or defining one or more value sets 38 for each parameter set 36. As described above, each parameter set 36 may include both time-invariant and time-varying parameters.

At block 84, a first simulation operation (e.g., experiment 14) is performed utilizing an initial simulation input (e.g., the configuration 60) to generate a first set of results for the time-varying parameters over time 65 (e.g., the experiment results 44).

At block 86, a modeler defines a delta simulation input, or inputs. Each delta simulation input may, for example, comprise a subset of a configuration 60 for a further experiment 16, while specifying the retention or inheritance of a further subset of a configuration 60 from the output of a preceding experiment 14 and a time N for retrieving the results from a preceding experiment 14. Each delta input accordingly may include a delta value set for a subset of values of a parameter set of a further experiment 16. Further details regarding how such a delta input (e.g., a further experiment 16) may be defined will be provided below where a discussion of an exemplary experiment interface 22 is provided.

At block 88, the system model 10 applies the delta input by, for example, commencing a further experiment 16 upon conclusion of a preceding experiment 14. The application of the delta simulation input may comprise automatically or manually copying the time-invariant parameter values from a preceding experiment 14, then automatically or manually copying at time N from the experiment results 44 of a preceding experiment 14, and finally utilizing the delta value set to generate the time-invariant parameter values 62 and time-varying parameter initial values 64 in the system model 10. In other words, the new values constitute a configuration 60 for a further experiment 16.

Figure 6:
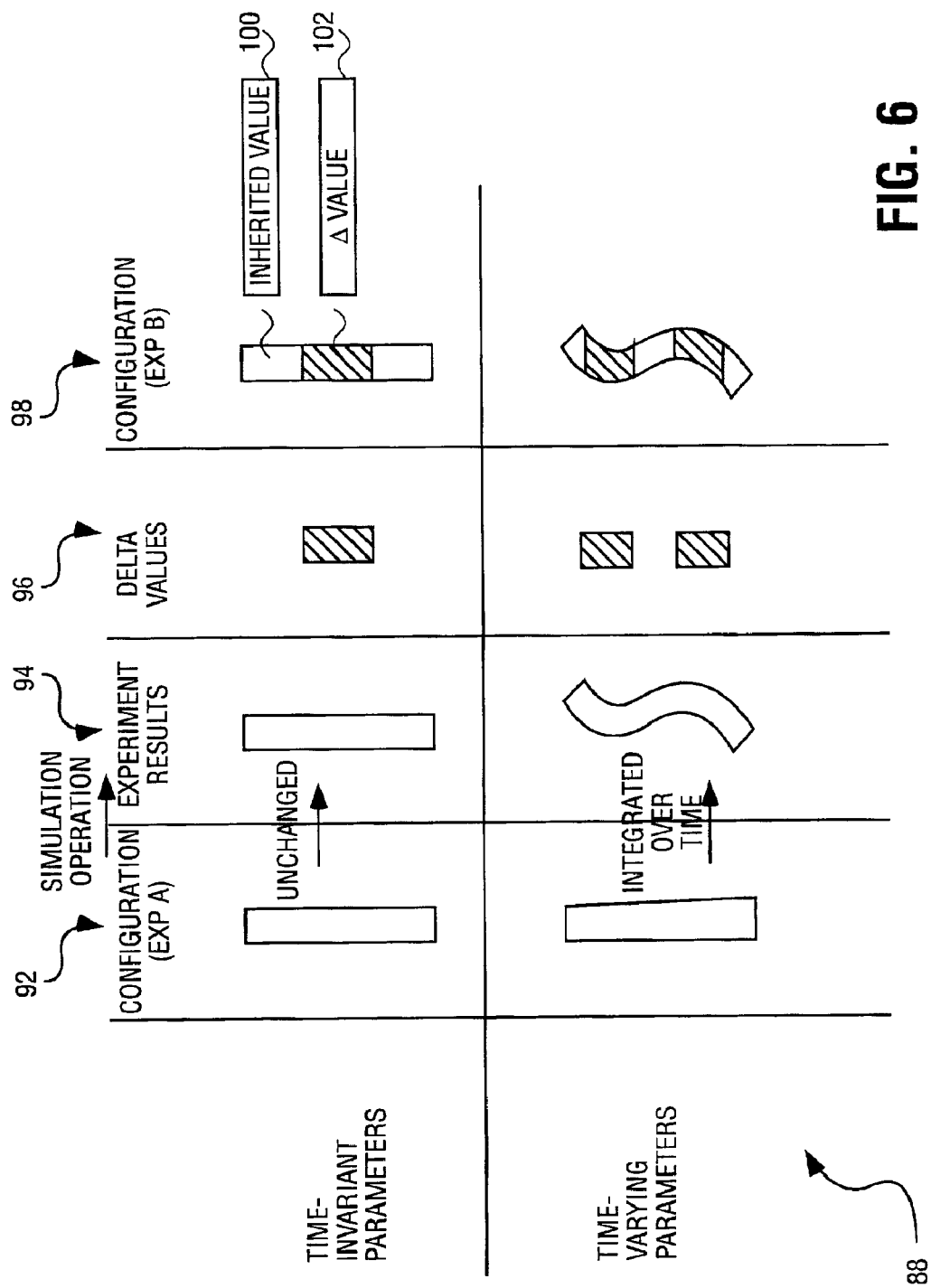
FIG. 6 is a diagrammatic representation of an exemplary modification operation that may be performed to apply a set of delta simulation inputs to the results of a preceding simulation operation.

FIG. 6 is a diagrammatic representation of an exemplary modification operation that may be performed at block 88 discussed with reference to FIG. 5. FIG. 6 diagrammatically illustrates various settings of parameters in the system model 10, and the modification of these parameters. Each setting is shown to include both time-invariant parameters and time-varying parameters. A configuration (experiment A) 92 comprise the configuration 60 for an initial experiment 14, and a first set of parameter values in the form of experiment results (experiment A) 94 comprise the experiment results 44 of the initial experiment 14. As illustrated, the values for the time-invariant parameters remain unchanged, whereas the values for the time-varying parameters vary over time (e.g., are integrated over time).

A set of delta values 96 are combined with the experiment results (experiment A) 94 to create a second value set of parameter values in the form of a configuration (experiment B) 98 that constitutes the configuration for a subsequent experiment 16. The manner by which the experiment results (experiment A) 94 and the delta values 96 may be combined may vary. In one embodiment, the time-invariant parameters and time-varying parameters are set to the experiment results (experiment A) 94. The delta values 96 are then applied, overwriting the corresponding values from the experiment results (experiment A) 94 to create the configuration (experiment B) 98. In this example, the configuration (experiment B) 98 thus contains both an inherited component 100 and a delta value component 102. It will of course be appreciated that the experiment results (experiment A) 94 may be modified in a number of ways by the delta values 96 to generate the configuration (experiment B) 98.

Returning to FIG. 5, at block 90, the system model 10 performs one or more simulation operations (e.g., subsequent experiments 16), the further simulation operations being sequential to the first simulation operation performed at block 84. As was described above, the further simulation operations utilize the configuration (experiment B) 98 as a part of their configuration.

While the operations described at blocks 82–90 are shown to be sequential, it will be appreciated that FIG. 5 should not be interpreted as requiring any specific order to the relevant operations. For example, the defining of the delta simulation inputs at block 86 may be performed at any time prior to the modification of the first value set.

Figure 7:
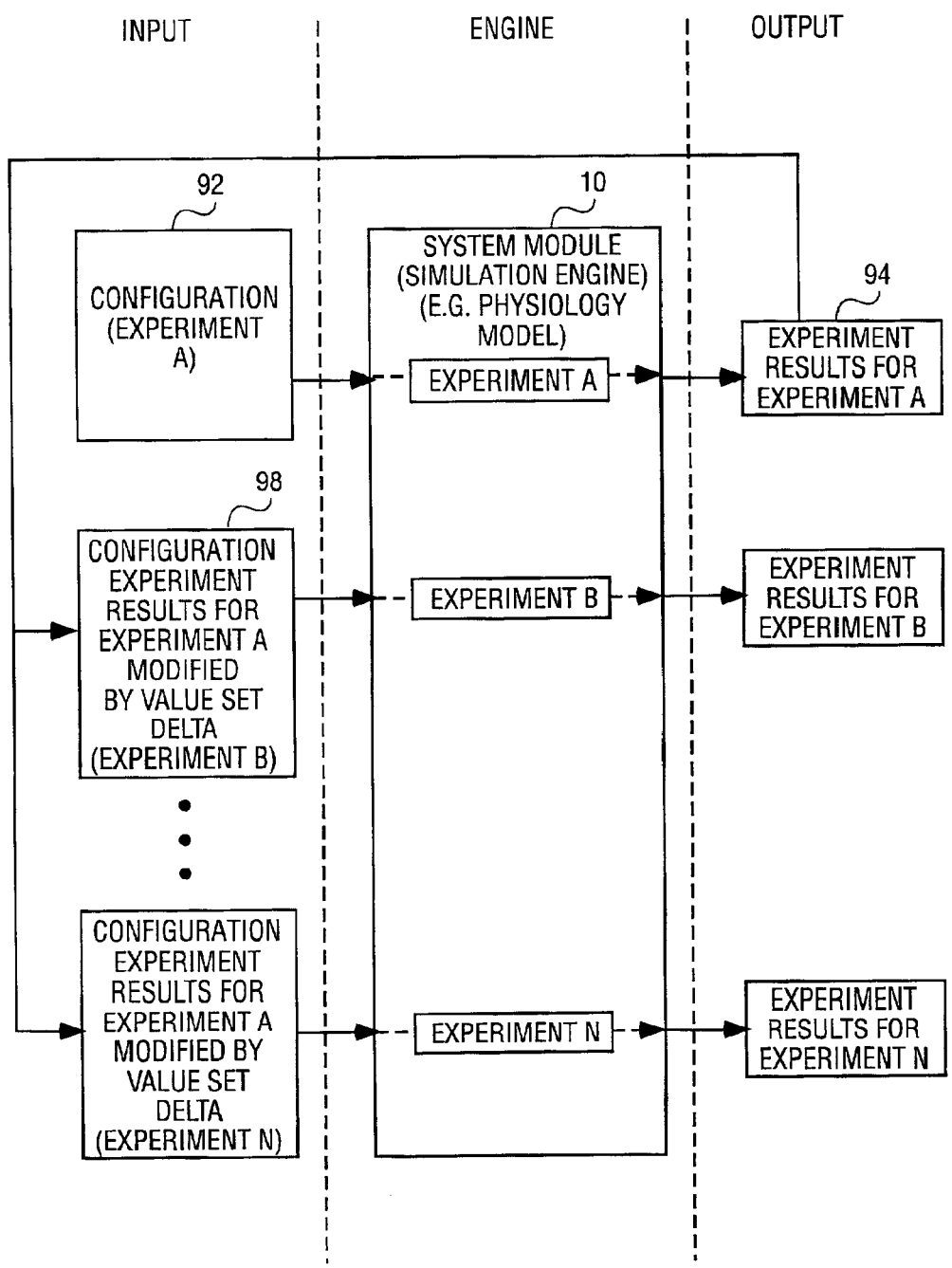
FIG. 7 is a block diagram illustrating the input and output of parameter values with respect to the system model.

FIG. 7 is a block diagram illustrating the input and output of the various parameter values with respect to system model 10. Specifically, FIG. 7 illustrates that the experiment results (experiment A) 94, outputted as a result of a first experiment 14 may be utilized to contribute to the configuration of any number of further experiments.

Figure 8:
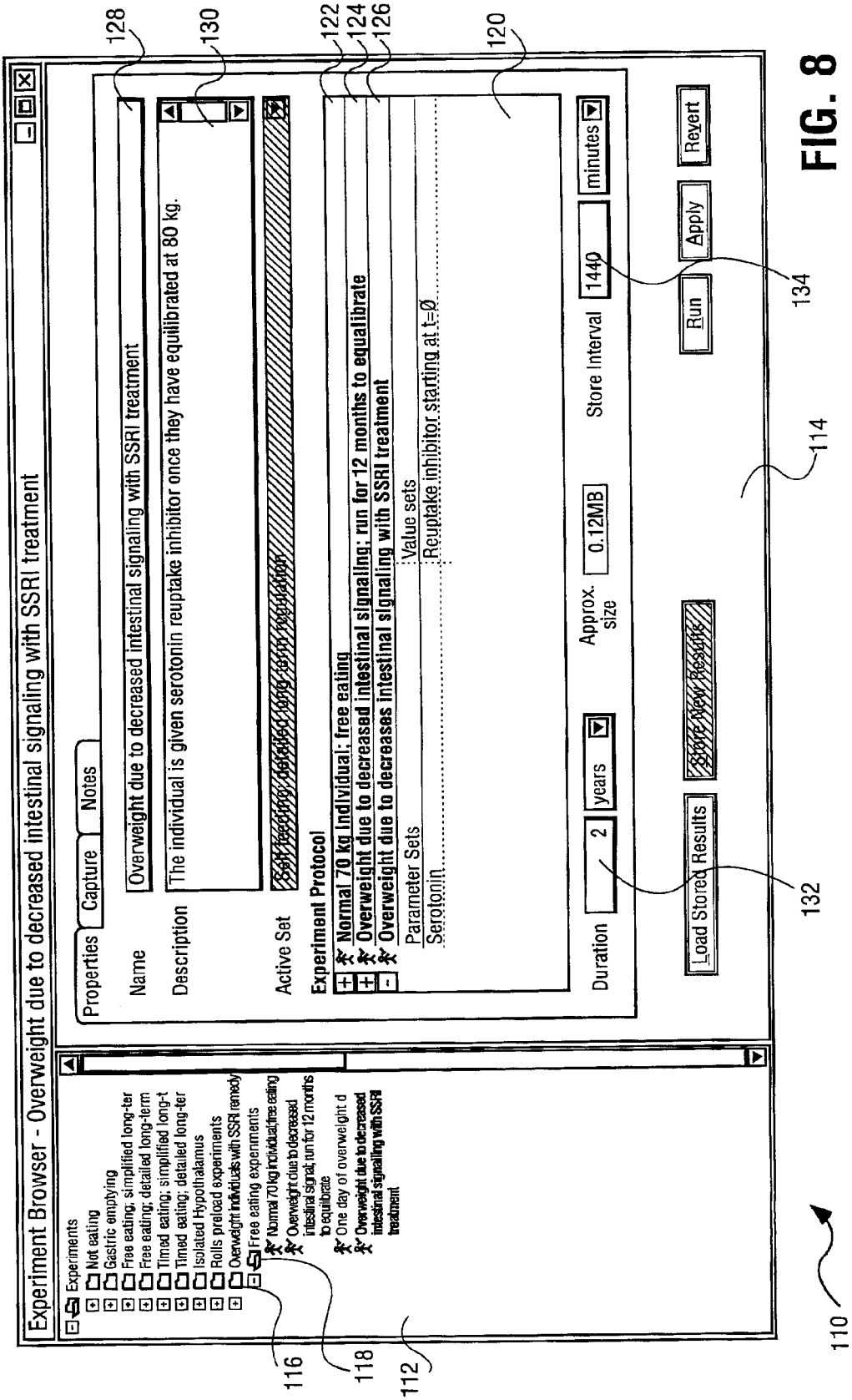
FIG. 8 shows an exemplary user interface that may be presented by an experiment interface of a system model.

FIG. 8 shows an exemplary user interface 110 that may be presented by the experiment interface 22 of the system model 10. The user interface 110 includes a directory panel 112 and input panel 114. The directory panel 112 provides a directory listing of various simulation operations in the form of experiments that may be transferred to the input panel 114 by a "drag-and-drop" or any other user-selection operation. The exemplary experiments shown in the directory panel 112 each specify a distinct physiological experiment and are appropriately categorizing into a number of "folders". The experiments that will be discussed in the following examples are experiments specified as relating to "Overweight Individuals with SSRI remedy" contained within the folder 116, and within the sub-folder "Free Eating Experiments" 118.

The input panel 114 includes an experiment protocol window 120 within which an experiment sequence designer may identify a group of experiments to be performed, as well as the sequence in which these experiments are to be performed. For example, FIG. 8 illustrates that by "dragging-and-dropping" experiments from the directory panel 112 into the experiment protocol window 120, the modeler has selected three experiments 122, 124 and 126 to be conducted in that sequence.

Further information regarding a selected experiment within the experiment protocol window 120 is shown within the name field 128, the description field 130, the duration field 132, and a store interval field 134.

Figure 9:
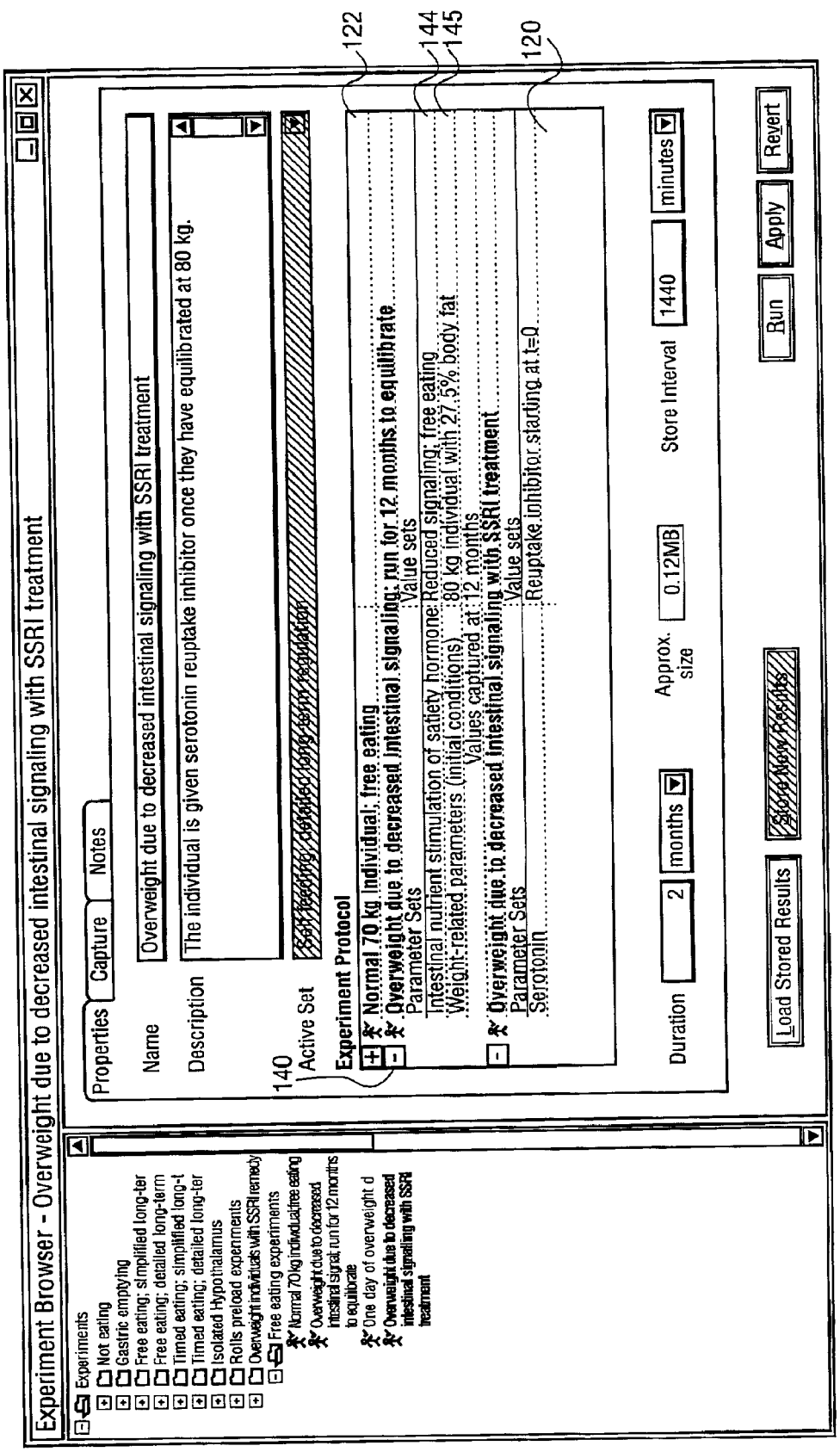
FIG. 9 illustrates a further view of the exemplary user interface shown in FIG. 8, where the protocol of a sequence of experiments has been partially expanded by user selection of an expansion button to provide further information regarding such experiments.

FIG. 9 shows the exemplary user interface 110, where the protocol of the sequence of experiments within the experiment protocol window 120 has been partially expanded by user selection of an expansion button 140 provided within the window 120 for each experiment. The expanded view of each experiment provides a list of parameter sets 36 for the relevant experiment, as well as indicating value sets 38 for each parameter set 36. For example, the "Overweight due to decreased intestinal signaling; run for 12 months to equilibrate" experiment 144 is shown to include a total of two parameter sets 36, each parameter set 36 having a value set 38 specifying predetermined conditions. One of these parameter sets 36 is the "weight related parameters (initial conditions)" parameter set 142 having a "80 kg individual with 27.5% body fat" value set 145 attributed thereto.

Figure 10:
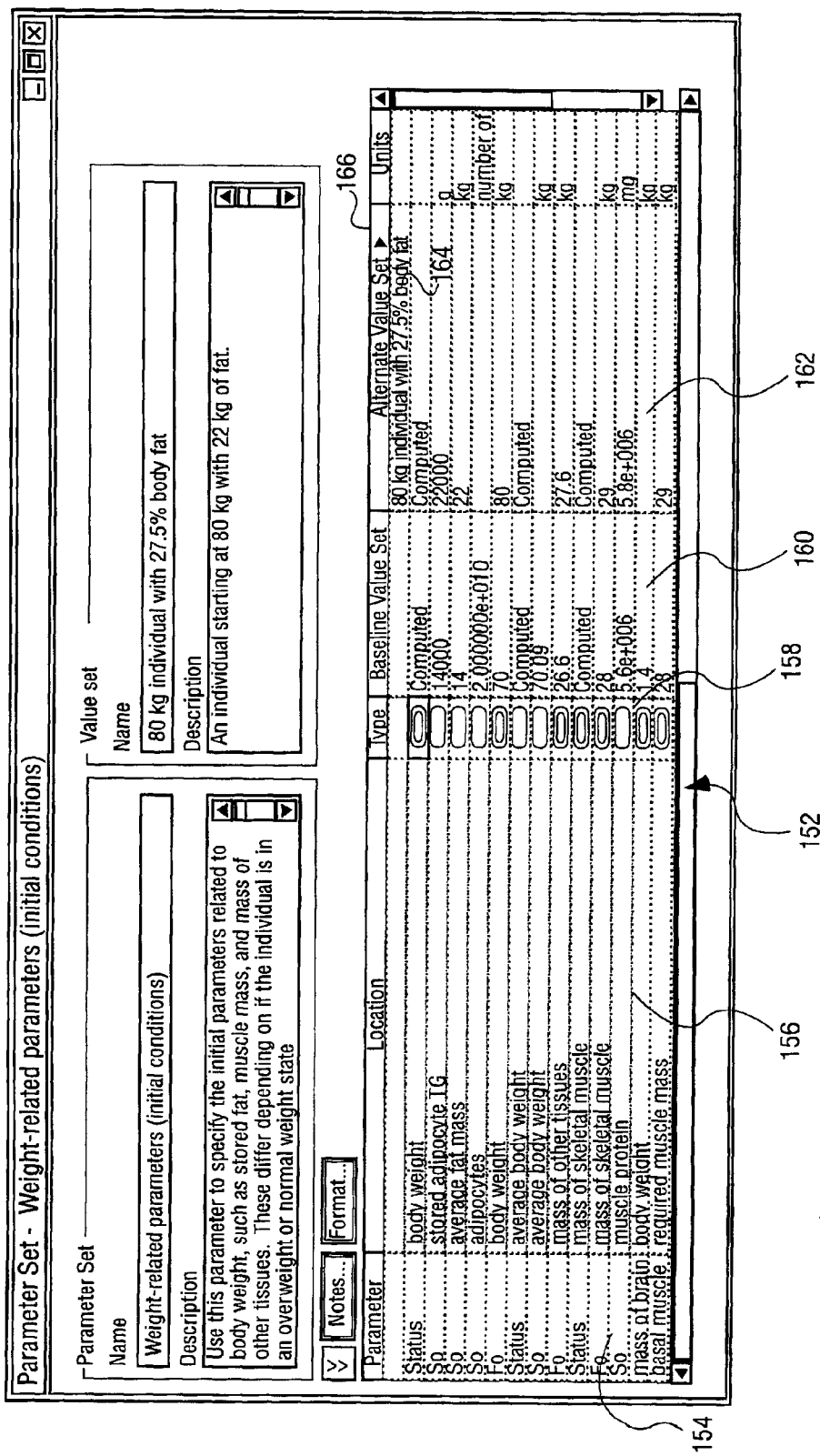
FIG. 10 illustrates an exemplary parameter set user interface.

User-selection (e.g., by double-clicking) on the listed parameter set 142 within the experiment protocol window 120 may, in one embodiment, generate the parameter set user interface 150 illustrated in FIG. 10. The parameter set user interface 150 lists both the parameter set and the value set associated with the parameter set for the relevant experiment. A parameter window 152 provides a listing of parameters included within the relevant parameter set 142, as well as values within the value set 144 attributed to the parameter set 142. The exemplary parameter window 152 is shown to include a parameter column 154, a location column 156, a type column 158, a baseline value column 160 and an alternative value set column 162. For each parameter, an entry within the parameter column 154 in the location column 156 provide an identifier, or designator, for the relevant parameter.

For example, the designator "So" identifies the relevant parameter as being the initial value for a "state" variable for which the value is determined by a cumulative effect of its inputs over time. A state variable may be defined by a differential equation, and is attributed an initial value that is indicated in either the baseline value set column 160 or the alternate value set column 162.

The type column 158 provides a visual icon, or other indicia, indicating the type (i.e., state or function) of the object containing the parameter.

The parameter set user interface 150 further allows an experiment designer to include new variables within a relative parameter set 36. This is done through, for example, dragging objects from the system model 10 onto the parameter window 152. Alternate value sets for this parameter set may be selected by clicking on the value set name popup menu 164 and may be created by clicking on the alternate value set popup menu 166.

Figure 11:
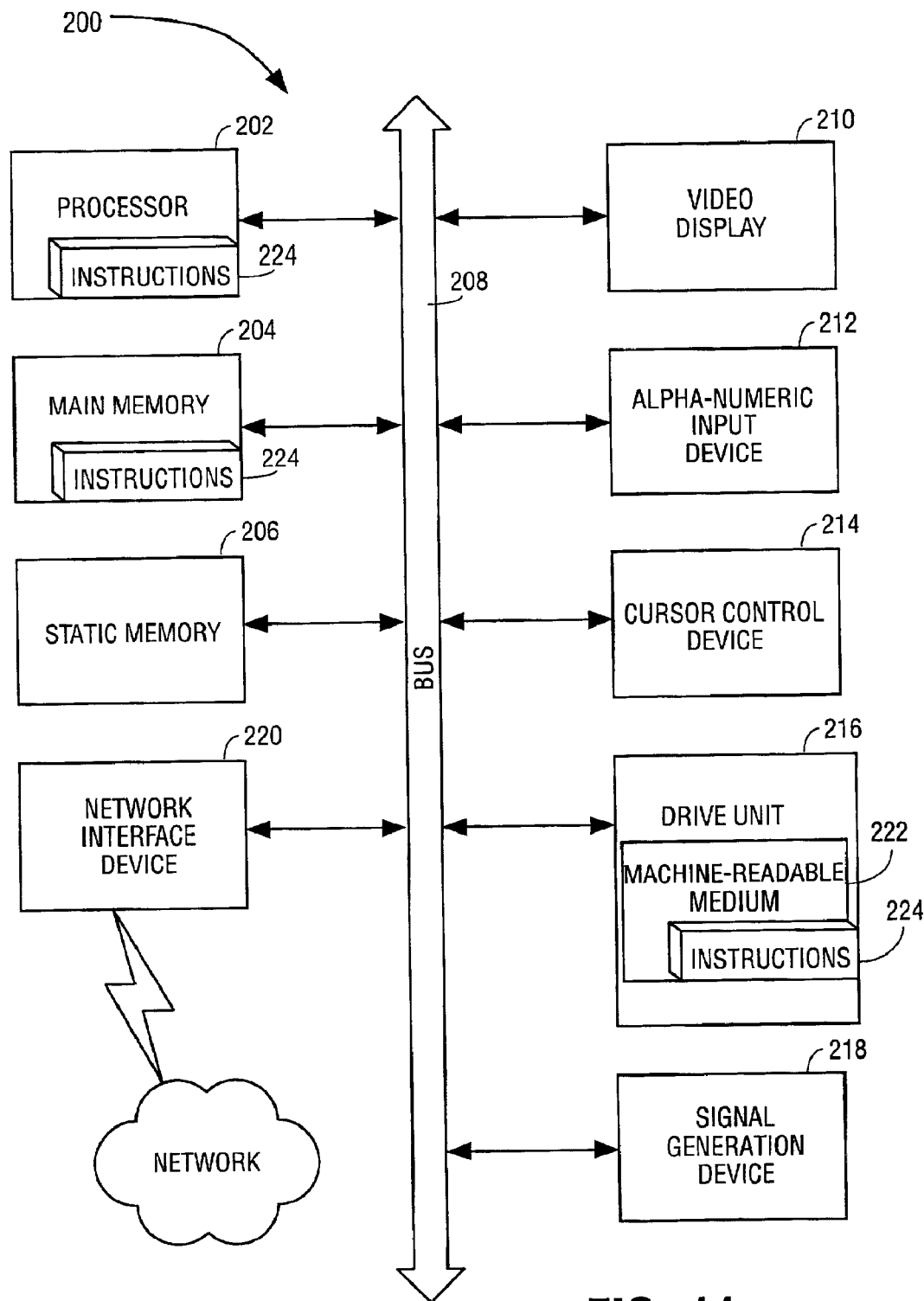
FIG. 11 provides a diagrammatic representation of a machine in the exemplary form of a computer system within which a set of instructions, for causing the machine to perform any one of a number of methodologies, may be executed.

FIG. 11 shows a diagrammatic representation of machine in the exemplary form of a computer system 200 within which a set of instructions, for causing the machine to perform any one of the methodologies discussed above, may be executed. In alternative embodiments, the machine may comprise a network router, a network switch, a network bridge, Personal Digital Assistant (PDA), a cellular telephone, a web appliance or any machine capable of executing a sequence of instructions that specify actions to be taken by that machine.

The computer system 200 includes a processor 202, a main memory 204 and a static memory 206, which communicate with each other via a bus 208. The computer system 200 may further include a video display unit 210 (e.g., a liquid crystal display (LCD) or a cathode ray tube (CRT)). The computer system 200 also includes an alphanumeric input device 212 (e.g., a keyboard), a cursor control device 214 (e.g., a mouse), a disk drive unit 216, a signal generation device 218 (e.g., a speaker) and a network interface device 220.

The disk drive unit 216 includes a machine-readable medium 222 on which is stored a set of instructions (i.e., software) 224 embodying any one, or all, of the methodologies described above. The software 224 is also shown to reside, completely or at least partially, within the main memory 204 and/or within the processor 202. The software 224 may further be transmitted or received via the network interface device 220. For the purposes of this specification, the term "machine-readable medium" shall be taken to include any medium that is capable of storing or encoding a sequence of instructions for execution by the machine and that cause the machine to perform any one of the methodologies of the present invention. The term "machine-readable medium" shall accordingly be taken to included, but not be limited to, solid-state memories, optical and magnetic disks, and carrier wave signals.

Thus, a method and apparatus for designing and conducting a sequence of linked simulation operations have been described. Although the present invention has been described with reference to specific exemplary embodiments, it will be evident that various modifications and changes may be made to these embodiments without departing from the broader spirit and scope of the invention. Accordingly, the specification and drawings are to be regarded in an illustrative rather than a restrictive sense.

What is claimed is:

1. A method of conducting a sequence of linked simulation operations utilizing a computer-based model, the method including:

performing a first simulation operation utilizing the model to generate an output condition; and performing a plurality of further simulation operations utilizing the model, wherein each of the plurality of further simulation operations, at least partially and automatically, inherits the output condition generated by the first simulation operation as an input condition, wherein at least one of the plurality of further simulation operations utilizes a delta condition in conjunction with the output condition of the first simulation operation as the input condition.

2. The method of claim 1 including presenting a model operator with a choice of performing at least one of the plurality of further simulation operations utilizing the delta condition in conjunction with a subset of the output condition as the input condition, and performing the at least one of the plurality of further simulation operations utilizing only the output condition as the input condition.

3. A method of conducting sequential simulation operations utilizing a computer-based system model, the method including:

performing a first simulation operation utilizing the system model to generate a first set of values for a set of model parameters;

attributing a delta value to at least a first model parameter of the set of model parameters, and maintaining at least an inherited value from the first set of values for a second model parameter to thereby generate a second set of values for the set of model parameters; and performing a second simulation operation utilizing the system model and the second set of values as an input condition.

4. The method of claim 3 wherein the first model parameter is a time-invariant parameter for which a value remains constant during a simulation operation.

5. The method of claim 3 wherein the first model variable is a time-varying variable for which a value varies during a simulation operation in accordance with specifications of the system model.

6. The method of claim 3 including attributing at least a further delta value to at least the first model parameter of the set of model parameters and maintaining the inherited value from the first set of values for the second model parameter to thereby generate a third set of values for the set of model parameters, and performing a third simulation operation utilizing the system model and the third set of values as a further input condition.

7. The method of claim 3 including attributing a first group of delta values to a first group of model parameters, and maintaining a first group of inherited values for a second group of model parameters to thereby generate the second set of parameters values for the set of model parameters.

8. The method of claim 7 including attributing a second group of delta values to a third group of model parameters and maintaining a second group of inherited values for a fourth group of model parameters to thereby generate a third set of parameter values for the set of model parameters.

9. The method of claim 3 wherein the first and second simulation operations are performed sequentially as a continuous simulation exercise.

10. The method of claim 9 wherein the delta value is automatically attributed to the first model parameter of the set of model parameters after the expiration of a specified time period and before conclusion of the continuous simulation exercise.

11. The method of claim 3 wherein the first simulation operation simulates operation of a system represented by the system model for a specified time period.

12. The method of claim 11 including facilitating specification by a model operator of the specified time point at the end of which the first set of values for the set of model parameters are generated by the system model, where the specified time point is less than or equal to the specified time period for the first simulation operation.

13. The method of claim 3 wherein the first simulation operation simulates operation of a system represented by the system model for a specified event sequence.

14. The method of claim 3 wherein respective model conditions vary between the first and second simulation operations.

15. The method of claim 14 wherein a level of influence of a first model condition is varied between the first and second simulation operations.

16. The method of claim 14 wherein the first model condition is present within the first simulation operation and is absent within the second simulation operation.

17. The method of claim 15 wherein the first model condition is absent within the first simulation operation and is present within the second simulation operation.

18. The method of claim 14 wherein the model conditions are determined by values attributed to the set of model parameters.

19. A computer-based system for conducting a sequence of linked simulation operations, the system including:

a simulation engine to perform first and second simulation operations; and a sequence generator to identify the first and second simulation operations as being sequenced and automatically to generate an input condition for the second simulation operation that at least partially inherits an output condition of the first simulation operation, wherein the second simulation operation specifies a delta condition and wherein the sequence generator generates the input condition for the second simulation utilizing both the delta condition and the output condition of the first simulation.

20. A machine-readable medium storing a sequence of instructions that, when executed by a machine, cause the machine to perform the steps of:

performing a first simulation operation utilizing the model to generate an output condition; and performing a plurality of further simulation operations utilizing the model, wherein each of the plurality of further simulation operations, at least partially and automatically, inherits the output condition generated by the first simulation operation as an input condition, wherein at least one of the plurality of further simulation operations utilizes a delta condition in conjunction with the output condition of the first simulation operation as the input condition.

21. A method of generating a graphical plot for values of a parameter of a computer-based model, the method including:

performing a first simulation operation utilizing the model to generate a first set of values for the parameter;

performing a second simulation operation utilizing the model to generate a second set of values for the parameter, wherein the second simulation operation at least partially inherits an output condition of the first simulation operation as an input condition; and generating a graphical plot on a display device associated with a computer system, the graphical plot plotting the first and second sets of values for the parameter as an integrated plot.

22. The method of claim 21 including performing a third simulation operation utilizing the model to generate a third set of values for the parameter, wherein the third simulation operation at least partially inherits the output condition of the first simulation operation as an input condition, and generating the graphical plot to plot the first, second and third sets of values for the parameter.

23. The method of claim 22 wherein the first, second and third sets of values for the parameter are plotted against time, and the output condition of the first simulation operation that is at least partially inherited by the third simulation operation as an input condition is determined at a different time from when the output condition that the second simulation operation at least partially inherits as an input condition is determined.

* * * * *